(12) United States Patent
Armbruster et al.

(10) Patent No.: US 12,352,747 B2
(45) Date of Patent: Jul. 8, 2025

(54) SYSTEM FOR ANALYZING QUANTITATIVE LATERAL FLOW CHROMATOGRAPHY

(71) Applicant: Immundiagnostik AG, Bensheim (DE)

(72) Inventors: Franz Paul Armbruster, Bensheim (DE); Felix Walzer, Bensheim (DE); Ben John, Bensheim (DE)

(73) Assignee: Immundiagnostik AG, Bensheim (DE)

( * ) Notice: Subject to any disclaimer, the term of this patent is extended or adjusted under 35 U.S.C. 154(b) by 1058 days.

(21) Appl. No.: 17/052,375

(22) PCT Filed: May 7, 2019

(86) PCT No.: PCT/EP2019/061749
§ 371 (c)(1),
(2) Date: Nov. 2, 2020

(87) PCT Pub. No.: WO2019/215199
PCT Pub. Date: Nov. 14, 2019

(65) Prior Publication Data
US 2021/0172945 A1    Jun. 10, 2021

(30) Foreign Application Priority Data
May 7, 2018  (DE) ............... 10 2018 110 861.3

(51) Int. Cl.
*G01N 33/558* (2006.01)
*G01N 15/06* (2006.01)
*G01N 21/84* (2006.01)
*G01N 33/543* (2006.01)
*G01N 15/01* (2024.01)

(52) U.S. Cl.
CPC ... *G01N 33/54388* (2021.08); *G01N 15/0625* (2013.01); *G01N 21/8483* (2013.01); *G01N 15/01* (2024.01); *G01N 2015/0687* (2013.01)

(58) Field of Classification Search
None
See application file for complete search history.

(56) References Cited

U.S. PATENT DOCUMENTS

| | | | |
|---|---|---|---|
| 4,298,685 A | 11/1981 | Parikh et al. | |
| 5,212,063 A | 5/1993 | Ofenloch-Hähnle et al. | |
| 5,229,073 A | 7/1993 | Luo et al. | |
| 5,717,778 A | 2/1998 | Chu et al. | |
| 8,935,007 B2 | 1/2015 | Kloepfer et al. | |
| 9,350,956 B2 | 5/2016 | Quilter et al. | |
| 9,390,237 B2 | 7/2016 | Myers et al. | |
| 9,756,324 B1* | 9/2017 | Flanagan | H04N 23/90 |
| 2005/0203353 A1 | 9/2005 | Ma et al. | |
| 2006/0222567 A1 | 10/2006 | Kloepfer et al. | |
| 2009/0211345 A1 | 8/2009 | Nahm et al. | |
| 2010/0254581 A1 | 10/2010 | Neeser et al. | |
| 2014/0065647 A1 | 3/2014 | Mamenta | |
| 2015/0031412 A1 | 1/2015 | Quilter et al. | |
| 2015/0241358 A1 | 8/2015 | Burg et al. | |
| 2015/0286803 A1* | 10/2015 | Myers | G06T 7/0012 235/375 |
| 2015/0308961 A1 | 10/2015 | Burg et al. | |
| 2017/0242421 A1* | 8/2017 | Ghazizadeh | G01N 35/1095 |
| 2019/0086400 A1 | 3/2019 | Ehrenkranz | |

FOREIGN PATENT DOCUMENTS

| | | |
|---|---|---|
| CN | 1455242 A | 11/2003 |
| DE | 10 2008 028908 B3 | 12/2009 |
| EP | 1 184 666 | 3/2002 |
| EP | 0 291 194 B2 | 7/2003 |
| EP | 1 550 872 A2 | 7/2005 |
| EP | 1 605 249 B1 | 4/2014 |
| EP | 2 781 910 A1 | 9/2014 |
| EP | 2 835 643 A1 | 2/2015 |
| EP | 2 927 688 A1 | 10/2015 |
| EP | 2 646 809 B1 | 8/2018 |
| EP | 3 470 825 A1 | 4/2019 |
| FR | 3 028 317 A1 | 5/2016 |
| GB | 2 497 750 A | 6/2013 |
| JP | 5005743 B2 | 8/2012 |
| WO | WO 92/21975 A1 | 12/1992 |
| WO | WO 2003/058242 A2 | 7/2003 |
| WO | WO 2004/011942 A1 | 2/2004 |
| WO | WO 2005/066624 A1 | 7/2005 |
| WO | WO 2008/049083 A2 | 4/2008 |
| WO | WO 2013/122121 A1 | 8/2013 |

(Continued)

OTHER PUBLICATIONS

Eletu SD et al. Development of an extended-specificity multiplex immunoassay for detection of *Streptococcus pneumoniae* serotype-specific antigen in urine by use of human monoclonal antibodies. Clinical and Vaccine Immunology. Dec. 2017;24(12):e00262-17., 14 pages (Year: 2017).*

*Primary Examiner* — Ann Montgomery
(74) *Attorney, Agent, or Firm* — Blank Rome LLP

(57) ABSTRACT

An analyte testing system for quantifying the presence of an analyte in a speciment by lateral flow chromatography. The system comprises a test cassette (10) with a lateral flow chromatography and a mobile hand-held processor device (16) comprising a digital camera (16*a*), a source of light (16*b*) and a processor (16*c*), which software and hardware (16*c*) are configured to determine automatically the distance between camera and object and the measures of light in the region of interest of the lateral flow chromatography prior any retrieval of image data for further analysis and quantification of the visual signals.

11 Claims, 5 Drawing Sheets

(56) References Cited

FOREIGN PATENT DOCUMENTS

| | | |
|---|---|---|
| WO | WO 2013/158504 A1 | 10/2013 |
| WO | WO 2013/158505 A1 | 10/2013 |
| WO | WO 2014/025415 A2 | 2/2014 |
| WO | WO 2014/100715 A2 | 6/2014 |
| WO | WO 2016/166415 A1 | 10/2016 |

* cited by examiner

SYSTEM FOR ANALYZING QUANTITATIVE LATERAL FLOW CHROMATOGRAPHY

FIELD OF THE INVENTION

The present invention relates to systems comprising device and software for analysing and determining by the use of visible optical light the presence and content of an analyte in a test sample which has been subjected to chromatography, in particular lateral flow immunochromatography, as well as lateral flow tests adapted for being used with said system.

BACKGROUND OF THE INVENTION

Lateral flow immunochromatographic tests are widely used in analytics and diagnostics. The technology is based on a series of capillary beds such as pieces of porous filter papers or a porous material on a membrane which each have the capacity to transport fluid by capillary action. The first bed—the sample pad—acts as a sponge and can accept an excess of sample fluid. The fluid migrates to a second bed—the conjugate pad—containing conjugate, a dried immunoreactant coupled to a marker, which is in a salt-sugar matrix that contains everything for an optimized binding reaction between the target molecule and its immunoreactive partner. While the sample fluid dissolves the salt-sugar matrix, it also dissolves the labelled immunoreactant and in one combined transport action the sample and conjugate mix while flowing through the porous structure. In this way, the analyte binds to the labelled immunoreactant while migrating further through the third capillary bed. This material there has one or more zones (lines or bands) with a third immobilized capture molecule. By the time the sample-conjugate mix reaches these lines, analyte has been bound on the labelled immunoreactant to form an immunocomplex and the immobilized capture binds the immunocomplex. When more and more fluid has passed the lines, label accumulates and the zone-area changes colour. Typically, there are at least two zones, a distal one (control) that captures any label and, thereby, shows that reaction and technology worked fine, and a proximal test zone that contains a specific capture molecule. This test zone only captures labelled complexes onto which the target analyte molecule has been bound. After passing these reaction zones the fluid enters a water-adsorptive material, the wicking pad, that acts as a waste deposit. Lateral flow tests can operate as either competitive or as sandwich assays.

The result of a lateral flow assay is usually determined by a visual readout of the detectable signal. One or more detectable coloured lines within the display zone with capture sites indicate the presence of analyte in the sample, and the control line a successful immune reaction and chromatographic separation (cf. U.S. Pat. No. 5,229,073 B, DE10 2008 028908 B3). The number of capture sites that become detectable due to the immobilization of labelled analyte is proportional to the amount of analyte present in the test sample. The intensity of the lines in the detection zone can therefore be used to determine semi-quantitatively or quantitatively the concentration of the analyte in the sample. However, the intensity of the lines in the detection zone cannot be easily determined. This is influenced by the separation material, porosity, thickness of the separation layer, pH of buffer, ageing of the test, light conditions, eyesight, temperature and multiple other influencing factors. Thus, conventional lateral flow test devices produce analytical or semi-quantitative results only.

JP 5-5743 and WO 2013/122121 A1 describe a lateral flow immunoassay t comprising a referential zone with a first immobilized capture antibody, a test zone with immobilized capture and a third region with another immobilized capture substance. The third region is configured to serve as a positive control whether or not the test has been performed correctly. The referential zone has been set to the maximum amount of analyte that can be captured. WO 2003/058242 A2 discloses a lateral flow test for quantitative determination of an analyte in a test sample. The porous membrane which is in fluid communication with labelled immunoreactants defines a test zone and a calibration area. The calibration area further defines one or more regions (e.g. dots, lines, etc.) containing differing amounts of capture antibodies configured to bind labelled conjugates. As a result, generated calibration signals are compared (visually, quantitatively, and the like) to a test signal to determine the presence or quantity of an analyte in a test sample. The disclosed lateral flow assay methods, however, are not suitable in terms of allowing quantitative point-of-care diagnostics in hospitals or at home since they are not sufficiently accurate.

Results have traditionally been interpreted visually. Test and control lines however vary greatly in intensity resulting in highly subjective analyses. Even a positive result may be indicated by a faint signal line. In such circumstances, some operators may conclude that no test line is present while others may identify the presence of a test line. The issue is further clouded by assay strips which sometimes contain a high level of background that may be incorrectly identified as a positive test line. Thus, assay strips provide results which are at best semi-quantitative and interpretation of result is subject to variance and the person performing the assay. Their application is restricted since quantification cannot be performed accurately with the naked eye. As assay strip formats provide rapid results, are simple to operate and more cost-effective than conventional formats scanners for determining the optical intensity of the response lines have been developed (cf. CN1455242A, WO2005/066624A1, EP 2 927 688 A1, EP 2 835 643 A1, EP 1 605 249 B1, US20090211345).

U.S. Pat. No. 9,350,956 (US 2015/0031412 A1) discloses a method for capturing the results using a portable digital device. US 2010/0254581 A1 discloses capturing a digital image and analysing said digital image by a mobile phone which sends the image data to a remote server for analysis. U.S. Pat. No. 8,935,007 B2 (US 2006/0222567 A1) and US 2019/0086400 disclose analyte test devices for quantitative analysis wherein a smart phone with a digital camera takes an image of the test strip. The method comprises the use of an interface between camera lens, light source and test strip for obtaining a standardized digital image of the test strip. EP 2 646 809 B1 and EP 3 470 825 A1 describe a test system wherein the processor of the smart phone is configured to reject a digital image when a degree of error associated with any rotational misalignment or skew of the imaged test device is greater than a predetermined value. U.S. Pat. No. 9,390,237 B1 (US 2015/0286803 A1) claims a method for determining the response lines of a lateral flow test which comprises a perspective transform to a recorded image on basis of a location information associated with the test device. US 2017/0242421 discloses the capturing of a digital image which includes a inherent calibration pattern. The encoded calibration information is used to generate a new image for further analysis.

These methods and systems however produce erratic measurements when used with the plethora of different types of smart phones and digital camera devices which are nowadays on the market. The state of the art therefore represents a problem. It is an object to provide a method and system for performing a quantitative determination of an analyte in a lateral flow chromatography as a digital readout. The test device may be a lateral flow immunoassay as widely used in point-of-care diagnostices as well as clinical and medical diagnostics. The method shall be suitable for telemedicine as it may be in veterinary medicine, as well as for food control, environmental analytics and in other technical fields.

SUMMARY OF THE INVENTION

The objects are achieved by a test system as claimed in claim 1. Another aspect concerns software for mobile phones for use with the test system of claim 1. Preferred embodiments have been disclosed in the dependent claims.

The test system as described herein provides the advantage that transient image data are analysed which are free of non-correctable primary data instead of recorded digital images. Moreover, the transient images data are analysed for non-correctable image data prior recordal and in order to to be do be able to do so with the plethora of different types of smart phones and tablets, they transient images are prioritized and assessed in the region of interest only, say within the region containing the visible zones and the quantitative signal of the analyte. Convential methods examine the entire recorded picture which contains 10 to 50 times more data. This is very different to the prior art which systems first select and correct for a "nice entire picture" (good alignment, contrast, colours) of the entire test device which inavoidably comprises the recordal of non-correctable image data prior an assessment of the optical intensities of the visible zones which represent the content of the analyte in the test sample subjected to chromatography. By prioritizing on the transient image and the non-correctable image data within the region of interest, a data reduction can be achieved since the region of interest represents only a small portion of the entire digital image. Consequently, multiple transient images can be processed even in smart phones with limited internal memory and processing power. Moreover, of the 2 billion cameras manufactured for the phone and tablet market every year, more than half of them autofocus. One or more of the lenses in the camera are moved in or out using a microelectromechanical actuator while an algorithm calculates a figure of merit for the sharpness of image for that location of the lenses. The various in-built autofocus algorithm may therefore work conflicting to applications with post-processing algorithms for perspective transform or correction of sharpness or contrast. The system and method described in this application reduces the amount of transient image data which therefore allows an instant assessment of the measures of light within the region of interest prior recordal of the image data of the region of interest only. The measures of light reflected within the region of interest are primary optical data which cannot be subsequently corrected by an algorithm since they relate directly to the amount of analyte captured in the visible zones. As a sequence of transient images of the region of interest is analysed, images with poor measures of light reflected can be discarded which lowers the risk of erratic determinations. In other words, the described method analyses a video clip of transient images of the region of interest and analyses those images individually for its measures of light so that images with exceptional characteristics can be ignored. This is only possible by reducing the data on the analysed transient images as well as by making use of the camera characteristics.

The described objects are achieved by a system for determining the presence and content of an analyte in a test sample subjected to lateral flow chromatography, the system comprising a test device adapted to house a lateral flow test which test device further displays one or more reference images (e.g. QR code, bar code, signs or characters) and a region of interest (ROI), also described herein as display of the test strip, which display shows one or more visible zones such as bands or lines indicating the presence and content of the analyte (T) in said test sample and a control zone (C), and—in functional co-operation—a portable processor device, preferably a mobile phone comprising a digital camera and a source of light, wherein said processor is configured to process digital images captured by said camera and to represent an analytical result. Said processor is configured to analyse sequentially a plurality of transient digital images for the presence of one or more permanent reference images and, if found and correct, to determine the distance between the found reference image and the digital camera, and if within an accepted distance, said processor is configured to analyse each transient digital image for said region of interest, and if found; said processor is configured to examine each region of interest for its measures of reflected light; and if in line with predefined measures; said processor is configured to retrieve and save said transient digital image so that digital images only will be processed and analysed for the optical intensities of said visible zones (T, C) which are based on predefined light conditions. When taking the transient digital images the camera lens and the internal source of light (flash) must be within an accepted distance to the test device. The camera must be in a position not too close and not to far to the object. If the distance is short the flash would overexpose the object and wet portions on the test strip would be very reflective so that the region of interest could no longer be analysed. If the camera lens and the flash are too far from the object, the region of interest would not become sufficiently illuminated and most importantly, the region of interest would also become too small in size for further analysis. A predefined accepted distance is needed for obtaining a properly illuminated object as well as for obtaining a region of interest of roughly uniform and sufficient size for determination of the optical intensities of the test and controle zones (T, C). If the distance is found being within an acceptable range, the region of interest can further be easily identified by its distances to the location of the reference signs on the test device. The analysis of the transient digital image for its measures of light as described below can then be limited to the region of interest only. For this purpose, the distance between camera lens and object must be within an accepted distance which can be examined by a fast and simple algorithm on basis of the permanent reference sign on the test device. If this is the case, the region of interest can likewise be easily identified and derived by its known size and location with respect to the reference signs.

The processor is then configured to determine the measures of light reflected from the region of interest with respect to absolute brightness, brightness gradient, shadows and areas of dark pixels and combinations thereof. It is also functionally important that the processor is configured to retrieve and save multiple approved transient image data of the region of interest so that the optical intensities of said visible zones (T, C) can be determined from multiple or sets of light-approved image data. The latter improves greatly the confidence and quality of recorded image data.

In a preferred embodiment of the analyte test system, the saved digital images are further corrected for any degree of error associated with any rotational misalignment or skew prior a determination of optical intensities of the zones (T, C). This can be done on basis of the visible zones as those must be in parallel.

The analyte lateral flow test will be employed in a preferred embodiment with a predetermined amount of control to achieve a defined control zone (C) independently from the presence and content of the analyte in the test sample. The control may be for example an IgG or a chicken IgY which does not recognize or react with the analyte but which is bound at the control line. Thus, the control line will not vary in strength and its strength is independent from the amount of analyte in the test sample. In the alternative, a variance would occur in cases where the sample contained a relatively high amount of analyte. The analyte would be bound by the immunoreactive partner so that there would be less unbound immunoreactive partners available for becoming bound in the control zone. The control zone would then become less intense. This does not happen when a predetermined amount of control is added.

In a most preferred embodiment the processor is configured to determine the intensity ratios (T/C) of the zones (T, C) from a number of saved images and chooses a median ratio (T/C) for quantitative determination of the analyte in the test sample.

When the analyte testing system comprises a test device with a reference image with a machine-readable representation of data (QR-code or bar code) such a code may encode or provide access to characteristic data of the lateral flow test on a server, e.g. via internet or by a direct telephone line, which may be used to correlate the determined median intensity ratio (T/C) with a quantitative determination of the analyte in the test sample. In a preferred embodiment, the analyte testing system is therefore configured to exchange data and image data with a remote server.

The analyte test system may further comprise a processor which is configured to employ data on sharpness and contrast of a displayed reference image or data on the location of the displayed reference image to identify the location of the visible zones (T, C) within the region of interest.

The analyte testing system for assessing the presence of an analyte by lateral flow chromatography comprises a test cassette adapted to house a lateral flow chromatography strip. The strip displays after use one or more visible lines or bands or responsive zones which indicate the presence of the analyte in the test sample and a control. The test cassette may display one or more reference images such as a bar code or QR code, and/or signs and characters. The smart phone must comprise a digital camera, a flash and a processor. The processor is configured to process captured image data of said test cassette, said one or more reference images and of the visible lines, zones or bands for the analyte present in said sample and said control. The processor is adapted to analyze the image data first for one or more reference images to evaluate the distance between the digital camera and the reference image, and if within the predetermined range, said processor is configured to analyze thereafter said image data for the region of interest and/or signals of the visible control, and if found, said processor is configured to analyse said image data for the properties of the light reflected from said chromatography strip (region of interest), and that said processor is configured to reject any image data if the evaluation of any value associated with the properties of light reflected from said chromatography strip is outside a predetermined range so that only captured image data will be retrieved and saved for quantitative analysis of the analyte which image data have been pre-examined as good and valid with respect to the measures of the light reflected from the chromatography strip. The chromatography strip corresponds to region of interest.

Said processor may be configured to analyse the properties of the reflected light with respect to brightness gradient, absolute brightness, shadow, sharpness, absorbance, transmittance, contrast and combinations thereof. Multiple sets of valid image data may be retrieved and saved by the processor device and processed for selecting one set of image data for assessing and quantifying the signal for the analyte. More precisely, said mobile processor device may be configured to capture and retrieve an uneven number of sets of approved image data, preferably from 1 to 13, more preferably from 3 to 11 sets, most preferred from 5 to 9 sets, so that one set can be selected in accordance with a median value. That region of interest can then be used for assessing and quantifying the presence of the analyte in the test sample. The processor may of course also analyse each approved transient image for optical intensities of the visible zones and obtain median values for the T and C zones.

In another embodiment, the reference image may be selected from one or more of printed shapes, logos, bar codes, QR-codes, visible distance lines and dots, boundaries of the cassette, shaping and designs on the housing, chromatographic strip, control lines, shapes and designs on a casing. The reference images may be a data matrix (one or more bar codes or QR codes) comprising calibration information, batch number and/or expiration date of the test or the data needed to access a website which contains all technical data and calibration information on the lateral flow test. The smart phone may be capable of transmitting and receiving data from a remote processing device or server.

In one embodiment, said processor may be configured to determine an error value range with respect to the properties of light received from the region of interest on the test cassette, wherein the error value range is determined by comparing captured image data with predetermined properties of light reflected from the test cassette.

In another embodiment, said processor may be configured to add one or more pixel values in an acquired image region (region of interest) and to identify the location of signals for control and test sample. Said processor may be configured to perform peak searching within the acquired image region (region of interest), the processor being adapted to quantify the intensity of signals for control and test sample by calculating a peak height or peak area, so as to determine the concentration of analyte in the test sample. Said mobile processor device may be configured to employ contrasting colours or items of different proportions printed on a casing or the test cassette or both to compare image data captured by the mobile processing device. Most preferred is a conversion of the RGB data into a grayscale for further analysis and quantitation of the optical intensities of the visible zones (T, C).

In another embodiment, the analyte testing system may be adapted for determining calprotectin, vitamin D, luteinizing hormone, follicle stimulating hormone, chorionic gonadotropin, thyroid stimulating hormone, albumin, fecal occult blood, gluten immunogenic peptides, bladder cancer marker, *Mycobacterium tuberculosis, Mycobacterium bovis, Mycobacterium africanum, Helicobacter pylori*, influenza virus A and B, troponin I, Tinea unguium, ferritin, D-dimer, C-reactive protein, group A *Streptococcus*, group B *Streptococcus*, genetically modified organisms, allergens present in cereals and products thereof, chickpea and products thereof, peanut and products thereof, hazelnut and products thereof, macadamia and products thereof, mustard and products thereof, soya and products thereof, sesame and products thereof, walnut and products thereof, pistachio and products thereof, lupin and products thereof, celery and products thereof, fish and products thereof, crustaceans and products thereof.

Another aspect of the disclosure relates to a software for use in a mobile processor device with a digital camera, a source of light and a processor for assessing and quantifying the presence and content of an analyte in a test sample by lateral flow chromatography. Said software may comprise means for imaging a test cassette adapted to house a lateral flow chromatography strip and display one or more visible signals for the presence of analyte in the test sample as well as for control, which test cassette also displays one or more reference images, and wherein said software is configured to process images captured by said camera to obtain image data of said test cassette, said one or more reference images and the visible signals for the analyte present in said sample and for said control, wherein said software is configured to analyze said image data first for one or more reference images to evaluate the distance between the digital camera and the reference image, and if within the predetermined range said software is configured to analyze thereafter said image data for signals of the visible control, and if found said software is configured to analyze said image data for the properties of the light which is reflected from said chromatography strip, wherein said software is configured to reject any image when the evaluation of any value associated with the properties of light reflected from said chromatography strip is outside a predetermined range, so that only captured image data will be retrieved for quantitative analysis of the presence of the analyte, which image data have been pre-examined as good and valid with respect to the properties of the light reflected from the chromatography strip. Said software may be configured to analyze the properties of the light reflection with respect to brightness gradient, absolute brightness, shadow, sharpness, absorbance, contrast and combinations thereof.

A preferred embodiment concerns a software for use in a mobile phone comprising a digital camera, a source of light and a processor, which software supports the taking of digital images, the reading of machine-readable representations of data, an exchange of data and image data with a remote server, and a representation of information, data and test results on a display, wherein the software is configured to process sequentially a number of transient digital images and analyze each digital image for the presence of a reference image with machine-readable data and to determine the distance between said reference image and the digital camera (16a), and if found and acceptable, said software is configured to analyze each transient digital image for a region of interest, and if found, said software is configured to examine each region of interest for the measures of light reflected, and if absolute brightness, brightness gradient, areas of dark pixels are found acceptable; said software is configured to save the image data of said transient digital image for further analysis of the region of interest.

The software is preferably configured to determine the location and optical intensities of the visible zones (T, C) within the region of interest. It may be further configured to retrieve calibration data and other deposited data for a determination of a quantitative result of a test sample subjected to lateral flow chromatography.

The assessment of a visual signal for accurate quantification of an analyte requires first a determination of the distance between the lateral flow chromatography test and the camera, if done with a hand-held optical device, and second a determination of the light conditions on the imaged chromatography and/or test cassette. The image itself may be corrected in arrear as necessary, e.g. in terms of any rotational misalignment or skew, image stabilization, or with respect to the temperature of the light or any tonal data. Even the histogram of an image will be open to post-processing. In terms of a quantitative evaluation of the zones, the histogram or tonal data are of little help if there is a shadow in the region of interest as such a shadow cannot be removed automatically. Thus, the primary measure of light in the region of interest (on the chromatography strip) must be even and good before any reasonable evaluation and quantitative assessment of the zones for test and control. This can be achieved by pre-establishing applicable conditions based on measure of light reflection in the region of interest, say in the region with the colored bands or zones.

Once the software has determined that the (transient) image has adequate brightness and the distance is within the acceptable range, the transient image is retrieved and saved for post-production and quantitative assessment of the zones. The translation of accepted image data into data on the concentration of the analyte in the test sample can be carried out employing batch- or lot-specific calibration data. The result of the assessment can be stored and/or adequately presented on the screen of the hand-held camera device. The result may be presented on a display or presented with an interpretation. If the hand-held is a smart phone, the so determined concentration of the analyte in the sample may be transmitted to a supervising physician. This may also be obligatory for certain diagnostic analytes and tests. The instant system can advantageously be used in telemedicine and analysis of stool samples. The system relies and been adapted to the typical hardware of smart phones so that no external hardware is required other than the lateral flow test.

In essence, the present disclosure provides a hand-held analyte testing system which can be adapted to a plurality of different tests, analytes and test samples and matrices. The lateral flow test is no longer based on the subjective visual assessment nor on special equipment (holder, tripod, lamps, distance means, etc.) but can be done anywhere at any time with any probe. The analyte testing system offers more precise quantitative results in the hands of non-professionals since it automatically assesses the distance and relevant measure of light (brightness and brightness gradient) in the regional of interest of the lateral low chromatography.

The invention will be described with respect to its advantages, favorable embodiments and examples, which shall not be considered limiting. The scope of the invention has been described inter alia in the claims.

DETAILED DESCRIPTION OF THE EMBODIMENTS

Figure 1A:
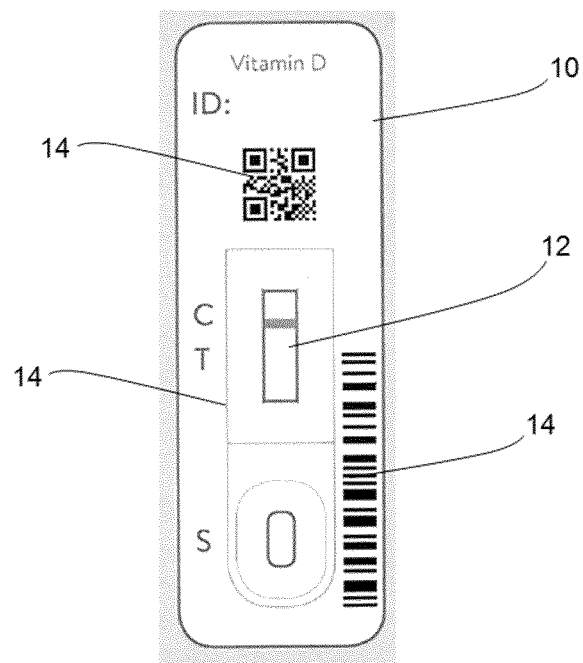
FIG. 1 A,B are schematic representations of the upper side of a test cassette which houses and presents various reference sign, a data matrix and the region of interest of a test strip for lateral flow chromatographic separation of an analyte (A—control; B—coloured analytic zone)

The disclosure relates to a system comprising a lateral flow test for use with a personal hand-held camera terminal (smart phone). The system has originally been designed to enable patients and physicians to evaluate objectively the result of a lateral flow chromatography performed on a biological specimen. A representative but difficult biological specimen is stool. Collecting a stool specimen can be a definitive step in determining the diagnosis and appropriate treatment for suspected infectious diarrhea and other gastrointestinal diseases. Stool specimens may also be required for non-microbiological testing, for example fecal immunological testing (FIT) or feacal occult blood tests (FOBT), an early detection method for colorectal cancer, or for proper monitoring the treatment of inflammatory gastrointestinal diseases such as coeliac disease. However, stool specimen collection is challenging, and stool sample are generally or only rarely collected at the doctor's office. Feedback from patients has indicated that they find the process difficult even though early fecal blood screening has been shown e.g. to reduce mortality. Generally, compliance is insufficient (rarely >60%) and reasons given for the lack of patient compliance include inadequate support for returning the collected specimen and embarrassment. It is fact that no patient wishes to drive a distance through their town or over land to handover a specimen of their fresh or frozen stool. Thus, remote analysis in the hands of the patients could represent a solution to these barriers. While the analyte testing system can be easily adapted to numerous other specimens, including food testing, and in other fields such as veterinary, agriculture, horticulture, environmental testing, drug testing, the instant disclosure will focus on the testing of stool as representative example which shall be considered non-limiting.

For analysis of the visual results, color information and/or gray values on the lateral flow test are analyzed via the camera integrated in a mobile phone or hand-held terminal, processed by an algorithm and then given as a numerical value, color code or text. Thus, patients or consumers can carry out such a quantitative lateral flow test themselves, receiving adequate information on the diagnosis or recommendations. In case of critical clinical parameters or analytes, the system may be adapted to and used in combination with automated certificates and authorizations so that the tests and analyses remain under the doctor's supervision. Thus, there may be analytes where simply the concentration of an analyte present in the sample is given and other where the result given to the user is that there is need to come to the doctor's office or hospital. Thus, a smart phone may be required for proper assessment of a disease or whereas the concentration of an allergen or contamination may be given as an absolute value of the analyte content in the sample.

The disclosure further pertains to a monitoring of health disorders, notably chronic gastrointestinal diseases, or an inflammatory status over longer periods of time and the effectiveness of a treatment or medication which may change with time. Results may be visually or numerically displayed as necessary and simultaneously sent to the supervising physician for telemedicine. The system may therefore provide considerable time savings to patients and doctors as unnecessary medical consultations can be avoided. It also reduces embarrassments around stool speciment collection and analysis

Definitions

In this context, the term "test cassette" refers to any kind of housing or envelope as typically used for a lateral flow chromatography strip. The test cassette may have a plurality of openings to allow an application of liquid with the test sample and a view port for the region displaying the results after separation. The term "test cassette" may also refer to a unit comprising a lateral flow chromatography strip or lateral flow immunoassay.

The term "processor" refers to electronic circuitry that carries out instructions of a computer program by performing arithmetic, logical, control and input/output (I/O) operations specified by the instructions.

The term "reference image" refers to any visually recognizable form, shape and/or data containing code such as, but not restricted to, printed corporate logos, captions, machine readable font, bar codes, QR codes, colour codes, batch designations as well as geometric elements such as distance lines and dots, boundaries, outside edges, inside edges, shaping designs, test, and control lines.

The term "visible signal" refers to any visually recognizable signal, colour, form, shape, geometric structure, line, dot, or response zone which appears on a lateral flow chromatography strip upon performance of a test reaction.

The term "control" refers to any visually recognizable signal, colour, form, shape, geometric structure, line, dot, or zone which confirms that a test has been performed correctly. The disclosure refers to a control zone on the lateral flow test. Conventional lateral flow tests use as control the binding of non-reacted analyte-specific antibodies. More precisely, a zone with immobilised antibodies recognising species- or class-specific antibodies, e.g. immobilised goat antibodies binding to monoclonal mouse anti-analyte antibody.

A preferred embodiment of the disclosure contemplates providing a defined amount of non-analyte specific antibodies in the application pad of the lateral flow test to obtain a control zone of predetermined intensity, an intensity which is independent from the amount of analyte present in the test sample. Consequently, the term "control" not only refers to the conventional control but comprises an "internal standard" for a standard intensity of the visual zone (C) for external and internal calibration.

The term "brightness" stands for an attribute of visual perception in which a source appears shining or reflecting light. In other words, brightness is in the instant disclosure the luminance flux or more precisely, the flux of light which is perceived when looking at the target. The target is in the present application the region of interest of the lateral flow chromatography, hereinafter described as viewport or region of visual interest. The term brightness as used herein comprises the color appearance of the test and control zones and the typically "white" chromatographic material on the membrane. As is well known, the light reflection or luminance of given target can elicit different perceptions of brightness in different contexts which is why the visual interpretation of the zones of a lateral flow chromatography cannot be easy. It may simply depend on whether the target is still wet or has dried and interpretation will depend on the surrounding light conditions and photographic shadows. Of the various color appearance models the inventors have preferably programmed the software using the RGB color space wherein brightness is the arithmetic mean of the red, green, and blue color coordinates although some of the components make the reflected light appear brighter than others. Most camera software make use of the RGB color space while there are alternative representations which align better with human vision. The latter however is not relevant for determining the intensity of the signal zones. While it would be nice to use the absolute magnitude of brightness or darkness of the signal zones, the relative values or the ratio between the test and the control zone are used. For determining the brightness of the viewport or region of interest, a further important parameter is the brightness gradient as the "absolute brightness" or luminance (reflected light) must be homogenous over the length and breadth of the region of interest. The brightness is determined by comparison of the brightness of various pixel areas in different regions of the viewport or region of interest. Moreover, the viewport is examined for shadows or untypical dark areas. Consequently, the examination of the brightness of the viewport, its brightness gradient and a search for untypical dark areas (photography shadows) is done on the transient image prior the image data are retrieved and saved for further processing and examination of the visual zones of the lateral flow test.

A shadow is a dark area where light from a light source is blocked by an opaque object. It occupies the volume behind an object being illuminated.

Sharpness (also "acutance") describes a visual perception related to the edge contrast of an image. Sharpness or acutance is related to the amplitude of the derivative of brightness with respect to space.

The term "absorption" as used herein refers to the physical process of absorbing light. Absorbance is the common logarithm of the ratio of incident to transmitted radiant power through a material. It measures attenuation of transmitted radiant power.

Transmittance of the surface of a material is its effectiveness in transmitting radiant energy.

Contrast in visual perception is the difference in appearance of two or more parts of a field seen simultaneously or successively.

The term "transient image" refers to transient data in the volatile memory of the processor for the assessment whether the transient image fulfils the primary condition of light reflection or brightness which allows correlation of image data with an analyte concentration in the test sample. The "transient image" will be cropped and the viewport excised prior retrieval and saving of the "image data." The cutting out of the relevant data will be done using the reference images (data matrix (QR code), bar code, marker lines, etc.) as those are in fixed or know spatial relation to the region of interest or viewport. The data matrix or bar code may also give access to the server for an exchange of data, notably calibration data.

The terms "retrieving", "acquiring", "recordal" or "saving" of image data refers to the process after having validated the image in terms of the measures of light (brightness, brightness gradient, shadows)—and taken from a test cassette that has not expired and for which calibration data can be found on the server.

The instant analyte testing system is made up of a software, preferably for a hand-held terminal with a camera or a smart phone, and a co-operating lateral flow test which have both been adapted and designed to meet legal, functional and practical requirements. As the smart phone will be the user's personal smart phone the method must work with the plethora of different types, generations and series of processors and camera devices. Each element of the test kit as well as the application software must therefore be tested with the user's personal smart phone or camera to avoid any harm to the user. The personal smart phone or camera must be checked first and this can be done for the instant system and method with a leaflet or card having printed thereon regions of interest with defined visible zones (T, C) as well as the permanent reference signs of the test devices. The camera and processor must be able to identify and analyse the region of interest as well as the printed intensities of the visible zones and only when this is performed correctly, the application software will identify the digital camera as approved and acceptable.

Thereafter, the software and/or smart phone may be configured to capture an image from a region of interest of a lateral flow test. For this purpose, the lateral flow strip may be placed in a cassette or envelope with specific openings for a defined application of the test sample and for a read-out of the results within a region of interest. The cassette, housing or envelope is a favourable embodiment for reasons of protection against fingerprints, etc, but no essential feature of the system. The software checks the transient image in respect of the distance between the object (lateral flow test) and the camera and the measures of light in the region of interest and in respect of a subsequent quantification of the analyte prior an image is actually retrieved and saved and subjected to further analysis and quantification of the colouring or optical intensities of the zones. Primary parameters for a quantification of the intensity of the colouring within the test and control zones are the distance and the light conditions in the region of interest on the lateral flow test. Those are relevant for determining the intensity of the visual signals (lines, bands or zones). The measured intensity in the area then relates to the amount of the analyte in question, provided the lateral flow test meets a number of standardizations. Those are lot and production dependent and needs to be determined in advance and carefully determined. A condition sine qua non is that the reproducibility of signal production multiplied with the reproducibility of the amount of sample applied onto the test strip is lower than the allowed error for the quantitation of the analyte. If these conditions are met and an internal reference provided by means of the control zone, the intensities of the test and control zones can be accurately determined even with a "simple" smart phone camera and the ratio of their intensities related to the amount or concentration of the analyte in the sample. The intensities of multiple zones can be used to increase the measurement range. It is easier from a manufacturer's point of view to have multiple test zones rather than controlling the zone breath. The machine-reading of reference images, more precisely of bar codes or data matrices (QR-code) can be used not only for assessing the distance and general light conditions but also for importing data such as lot number, date of expiry, calibration, etc., for further processing of the image and analysis. Accurate results can thereby be obtained, if the visible zones are well lit which is needed for a correct read-out of the signals. The distance between the hand-held camera (processor device) and the object (test cassette or region of interest) must also be as predefined and in the necessary range for a machine-evaluation of the received light on the image.

The present application provides a system and software whereby a mobile phone is upgraded to an analytical or diagnostic tool which provides guidance to users with no technological talent or expertise and can be used by anyone. The software may not merely perform a quantitative analysis of the bands or zones of a lateral flow test but may also give instructions on how to do the lateral flow test correctly and an a preanalytical preparation of a specific biological specimen. With the system of the disclosure, an analytical test can easily be performed at the point of care and the result imaged and quantified almost instantly and/or sent to a remote server. The result may also be passed on by the server to a general physician or medical centre and the server may also provide and/or check for the certificates required for telemedicine. The remote server may undertake an advanced image-processing analysis or provide diagnostic recommendations. The server may also pass on, return or save locally or in the cloud the analysed image and the report for reasons of quality control, statistics, etc. and may also save conditions, parameters or attribute associated with the sample tested (e.g., time, date, person, GPS data, personal data, and other details.

Figure 1B:
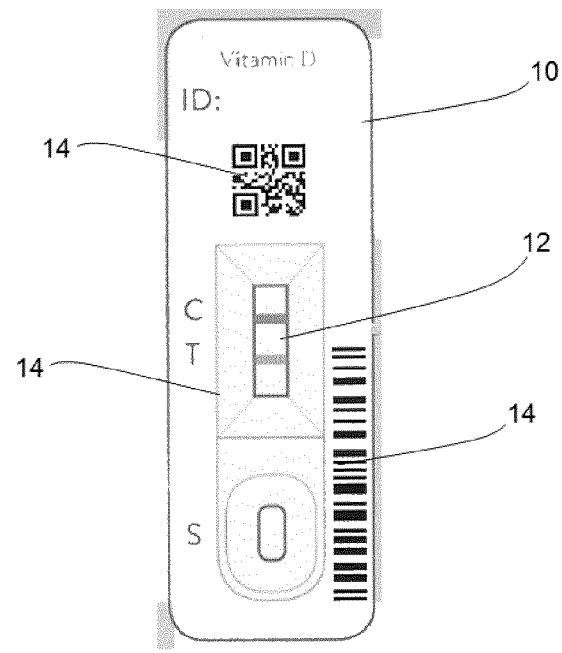

As shown in FIG. 1, the test cassette (10) has an opening for a region of interest or viewport (12) with visible zones for the control line (C) and a test line (T) (FIG. 1A, B). There may be multiple test lines (T) transvers the flow direction to enlarge the measurement range for the analyte. The upper side of the test cassette (10) displays further two types of reference images (14), a data matrix or QR code (top) and a bar code (lower right side). A defined amount of liquid with test sample may be added for chromatographic separation at spot (S) on the application pad.

Figure 2:
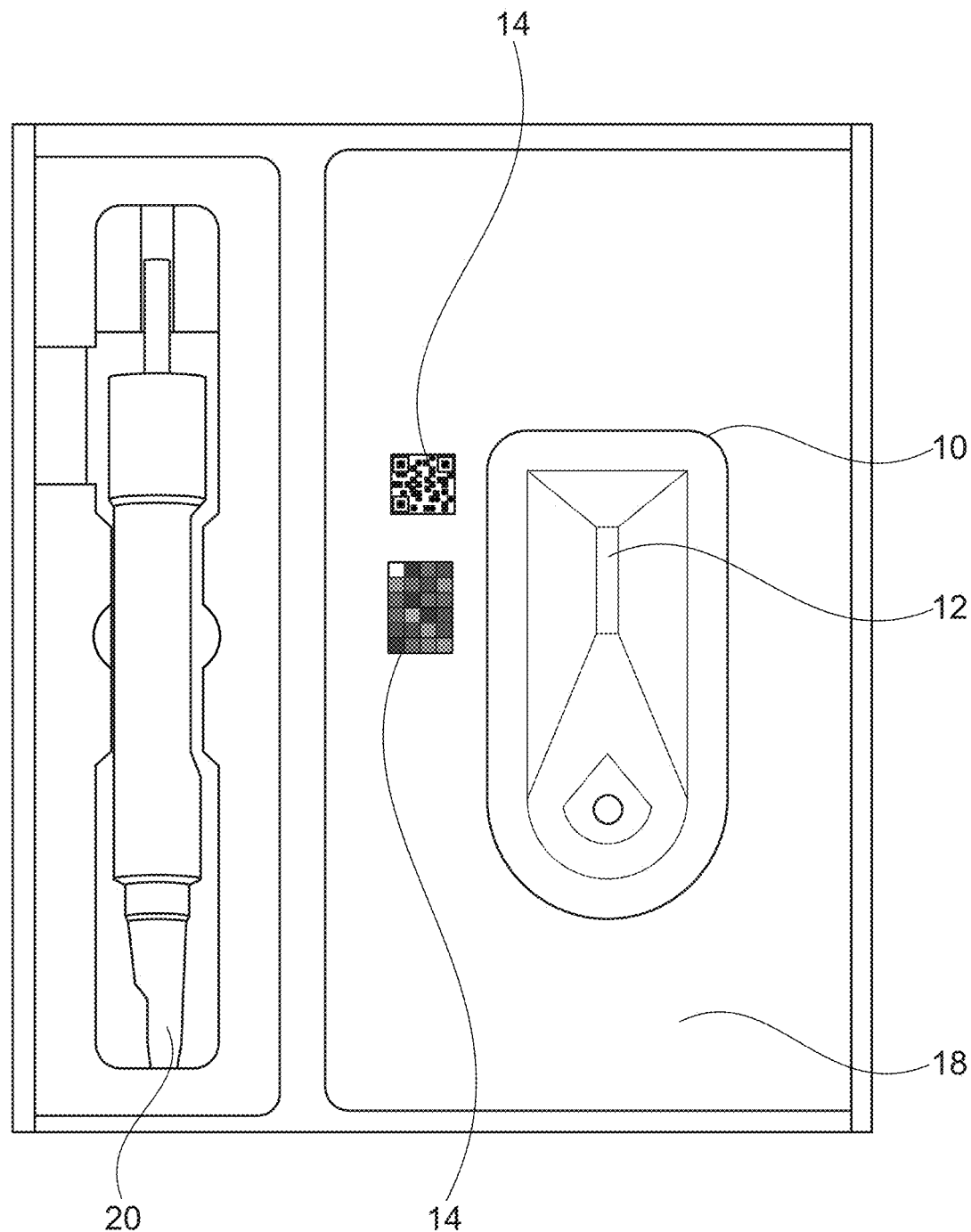
FIG. 2 is a photo of a typical sales box comprising the details for taking a defined stool sample, extraction of the stool matrix and application of a defined amount of stool extract onto a lateral flow test which is further analysed in accordance with instant disclosure.

A representative packaging is shown in FIG. 2. The test cassette (10) is integrated in a casing (18) which displays reference images (14), namely a QR code (centre, upper) and a colour/grey gradient (centre, lower), and accommodations for a device with reagent (20) for collecting and extracting a stool specimen. The viewport (12) with the region of interest of the lateral flow is located on the cassette.

Figure 3A:
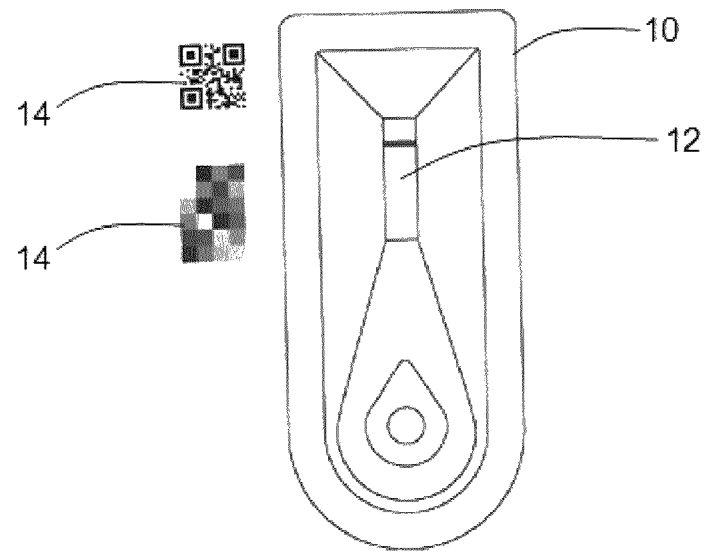
FIG. 3 A,B are schematic representations of the lateral flow test of FIG. 2 and corresponding reference signs and the data matrix with multiple analytic zones for an increased measurement range of the analyte.
Figure 3B:
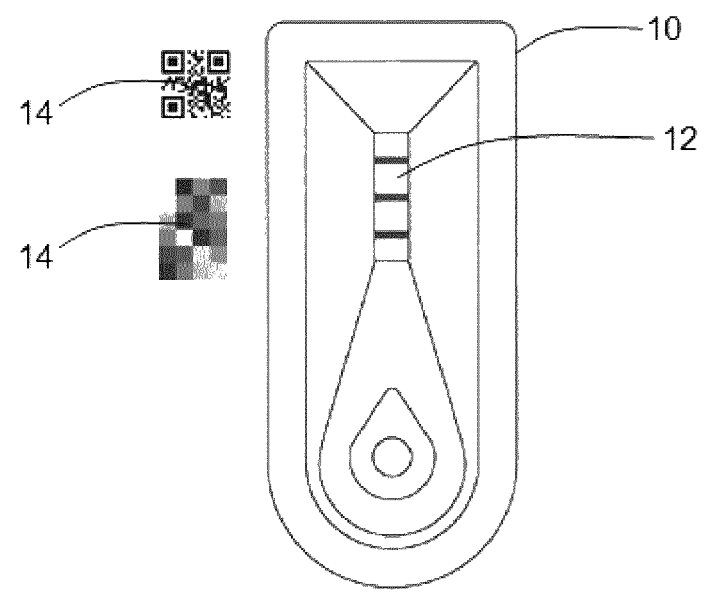

FIG. 3 shows a test cassette (10) with a region of interest or viewport (12) displaying a visible control (C) line only (FIG. 3A). FIG. 3B shows a test display or viewport (12) with plurality of visible test lines (FIG. 3B) to enlarge the measurement range. The reference images (14) are here again printed on the casing (20) as shown in FIG. 2.

Figure 4:
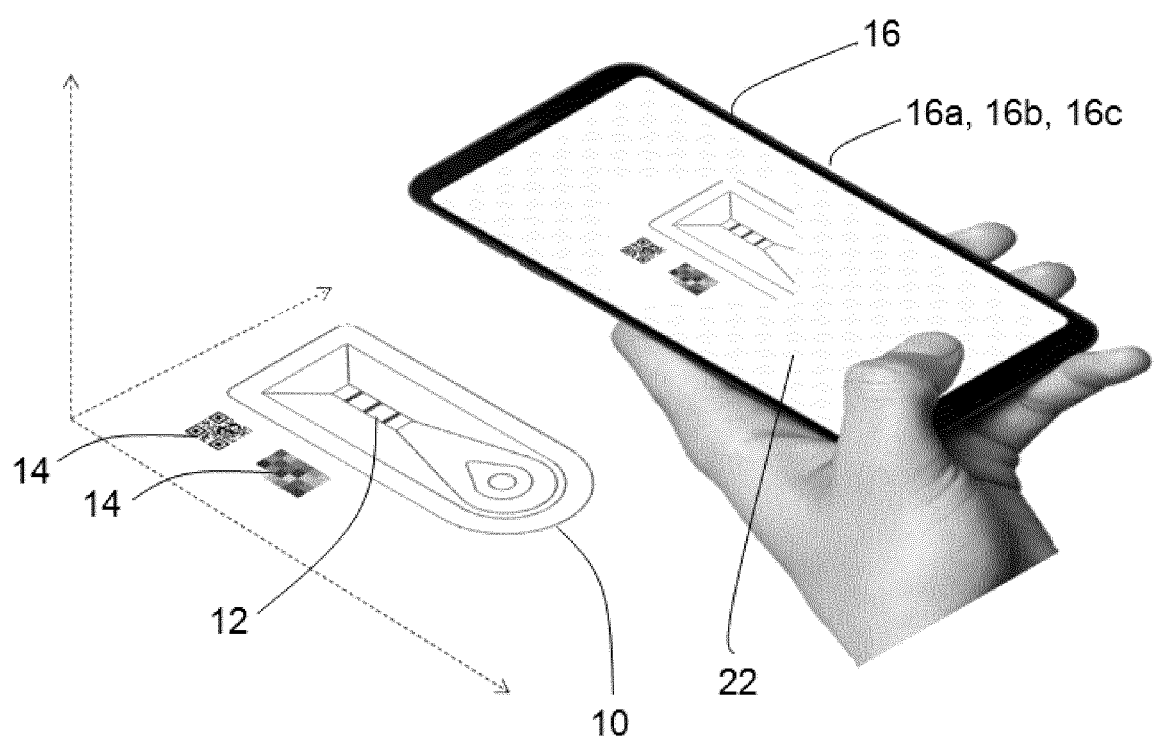
FIG. 4 shows a perspective view of the analyte testing system comprising a hand-held camera terminal (camera smart phone) and a lateral flow test as well as in cooperation therewith examples of a data matrix and reference signs.

As shown in FIG. 4 the test system comprises a test cassette (10) and a hand-held mobile processor device (16), e.g. a mobile phone (16) with a digital camera (16a) and a screen or display (22) for its user. The mobile phone (16) comprises a source of light (16b) and a processor (16c). The mobile phone (16) captures a transient image comprising the test step or viewport (12) and the reference images (14). The transient image can be viewed by the user on the display (22) of the smart phone (22) and if distance and the measures of light with the region of interest are correct, the image will be retrieved and saved by the mobile phone. In addition, the mobile phone (16) reads the data contained in the reference signs which provide data to access a server holding data for checking the lot number, expiration dates etc as well as calibration data for an analysis of retrieved and saved image data. The data for accessing the server may be provided in machine-readable form by the references images (14). The reference images—a QR code and a bar code are printed adjacent to test cassette (10) on the casing (18).

Figure 5:
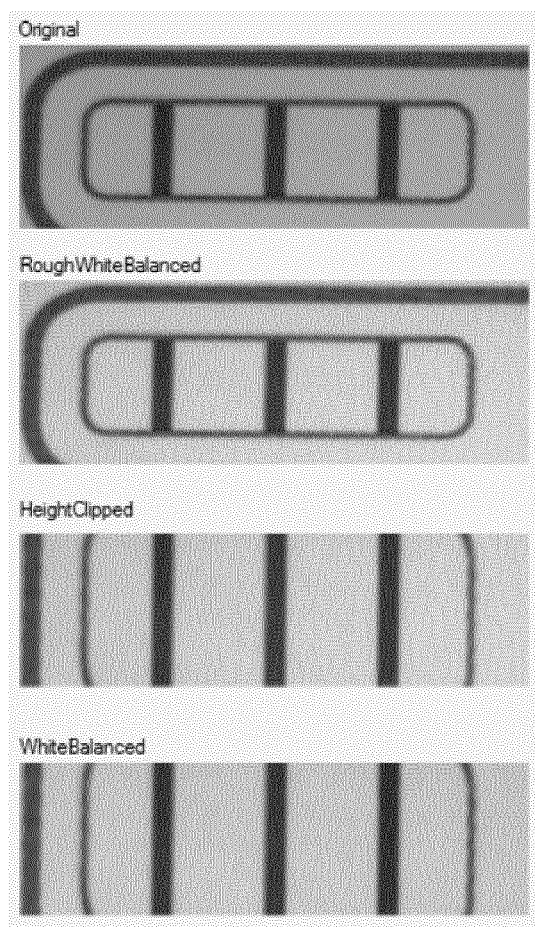
FIG. 5 shows a region of interest with visible zones (T,C) and schematically the additional processing steps prior analysis of the optical intensities of the visible zones (T, C) within the region of interest taken from the transient image, which ratio will be used for quantitative determination of the analyte in the test sample.

FIG. 5 shows how the region of interest (12) with visible zones (T,C) can be favourably processed prior analysis of the optical intensities of the visible zones (T, C). FIG. 5 shows, from top to bottom, the region of interest (Original) on the transient image as defined by its location and distance to the reference images (14). The measures of light reflected of the region of interest are determined, and if found acceptable, the data of the transient region of interest are subjected to a rough white balance (RoughWhiteBalanced) and then cropped on the side to a predefined width (HeightClipped) which also removes any lateral inklination or skew. The so processed region of interest will then be subjected to a precise white balance with respect to red, green and blue (RGB) so that the optical intensities of the lines can be converted into grey scale (not shown). If necessary, any rotational misalignment of the T, C zones or lines will now be corrected as those lines must be in parallel and run in a defined direction to the reference images (14). By limiting the data analysis of the transient images to the area of the region of interest, a substantive data reduction is obtained so that the analysis can be done by most conventional processors without any noticeable delay. Multiple transient images can be analyzed therefore and the results of the optical intensities of the visible zones can be analysed statistically. In a most preferred embodiment the median values of the optical intensities of the T and C zones are determined from a little sequence of transient images (transient video clip). The T/C ratio of the medians is then correlated with a calibrated curve to determined the amount of analyte present in the sample.

The analysis of the visual zones (T, C) can preferably be done using the peak intensities. It turned out that the peak intensities are sufficiently precise while the inventors have also examined using the integral intensity or the Gaussian intensity of the zones. The peak ratio of the T and C zones proved best also with respect to calibration and correlation with the determined concentration of the analyte in the test sample. The correlation requires machine-readable data on the test device and/or the data hold on a server. The correlation data may comprise production information, batch number, production date, lot number, calibration information, and a calibration diagram, as well as other relevant data relating to the lateral flow test such as certificates for encoded transfer of confidential medical data, authorizations (whether or not the owner of the smart phone is entitled or trained to do the medical test), contact information, the name and address of the medical center or physician, etc. The data transmitted and exchanged with the server may be the diagnostic result which is also (obligatorily or not) passed on to the general physician, hospital, central data unit, government, etc. for legal and practical reasons or for reasons of quality control and statistical interpretation.

There is sometimes a need of continuously monitoring the levels of an analyte, e.g. for an inflammation marker such as faecal calprotectin. These parameters provide, if measured accurately, an understanding of the person's over-all health condition, and set the basis for an early intervention or ongoing medication. Conventional healthcare services are primarily concerned with the treatment of a disease or the monitoring of a medication. The medical focus is however turning to the monitoring and maintenance of a person's health prior to the onset of a disease. Healthcare expenses can be reduced, and quality of life increased by an effective prompt treatment of conditions, and by creating a reasoned basis for individuals to adopt changes in their lifestyle. This requires means for telemedicine as provided by the instant application.

Food analysis is also an important field due to the increasing occurrence of allergies. Also, certain consumer's choices must be met, e.g. avoidance of genetically modified food and organisms in processed foods. Consequently, there is a demand for accurate tests that can be used by individuals without involvement of specialized laboratories.

Lateral flow test devices have been developed for numerous analytical questions. The analyte may be any antigenic substance but is usually a biomolecule such as a protein, peptide, antibody, carbohydrate or metabolite, a pathogen, or a nucleic acid such as DNA, RNA, an oligo- and polynucleotide or a PCR product (cf. EP 0 291 194 B2 and references therein). With tremendous advantage hapten or hapten-like binding pairs have been used to indirectly bind members of a specific binding pair to carrier. The best-known examples of a hapten-like, non-immunological, binding pair is the biotin/avidin or biotin/streptavidin-system. Properties and advantages of biotin-(strept)avidin-systems are e.g. described or disclosed in U.S. Pat. No. 4,298,685 (Parikh et al.), U.S. Pat. No. 5,212,063 (Offenlock-Haehnle et al), WO 92/21975 A (Abbott Lab), EP 1184666 (Roche Diagnostics). The basic principles of lateral flow tests however pertain to all these tests. The method comprises a contacting of a liquid sample with a test system which may be a sample pad for receiving the liquid sample, a conjugate pad, a test membrane with a separation material and one or more test or control zones or lines containing an immobilized capture immunoreactant.

The test devices may have one or more test strips included in a test cassette with windows for sample application and reading out the results. The test devices may also be used with blood as a sample. The cellular components (e.g. red and white blood cells) may then be separated from plasma using a porosity or receptors binding RBC, granulocytes and thrombocytes as needed. The plasma may be reacted in the direction of flow with one or more reagents that are immobilized on the strip. The mobile immunoreactant may be conjugated with a visually detectable marker or enzyme, while latex or nano-sized particles of gold are most commonly used.

To overcome the "human factor" computerized readers or scanners have been developed. The so-called POCT readers use sophisticated hardware to acquire an image of the lateral flow test and perform a computerized analysis of the image. The conventional POCT readers, however, are too bulky and expensive for being used by the patient at home. In addition, conventional POCT readers are specifically configured to interpret the result of only some specific tests. If a doctor's office needs to conduct only a few tests a day or a plethora of different tests, it may be necessary to purchase different POCT devices (e.g., several POCT devices from different manufacturers) and multiple POCT readers are a too expensive option for individuals and general physicians. In addition, not only the test devices are lot dependent but also phone cameras and photo sensors in their optical properties. The instant disclosure allows the use of a camera check test on basis of a printed card which can be designed that unsuitable or broken phone cameras and smart phones can be excluded from performing the application and a read-out of the test device.

In general, the analyte testing system for assessing and quantifying the presence of an analyte in a sample by lateral flow chromatography consists of a test cassette which is adapted to house a lateral flow chromatography strip and display one or more visible zones for the presence of analyte (T) as well as for control (C) and internal standard. The test cassette may also display one or more reference images. The system further consists of a hand-held terminal comprising a digital camera, a source of light and a processor, wherein said processor (16c) is configured to process the transient images captured by said camera (16a) to examine said transient image data of said test cassette and said one or more reference images. Said processor is adapted to analyse said image data first for one or more reference images to evaluate the distance between the digital camera and the reference image, and if within the predetermined range said processor is configured to analyse said image data for measures of light (brightness, brightness gradient, luminance, shadows) in the region of interest or viewport. In other words, said processor is configured to analyse first said image for the properties of light reflected from said chromatography strip before performing any further analyses. Said processor is configured to reject or ignore all images when the evaluation of any value associated with the properties of light reflected from said chromatography strip is outside a predetermined range. Only image data will be retrieved for quantitative analysis which data have been pre-examined as good and valid with respect to the measures of the light reflected from the chromatography strip.

Referring to the Figures, the analyte testing system of the present invention comprises a test cassette (10) which displays one or more reference images (14). Those will be used for determining i) the distance between the hand-held terminal (16) and the test cassette (10), and optionally ii) whether the machine-readable data indicate whether it is a valid test in terms of lot number and calibration data. The assessment whether an image can be used for quantification requires whether the determined distance between the test cassette (10) and the camera (16a) is in an accepted range and on the measures of light, more precisely a homogenous luminance within the region of interest (viewport) on the test cassette (10).

The software may be configured comprising an accepted error or variance range with respect to the properties of the reflected light (luminance). The primary parameters in this connection may be selected from the group comprising absolute brightness (luminance, reflection), brightness gradient within the region of interest (viewport), darkness or dark areas which correspond to photographic shadows in the region of interest. Secondary parameters comprise sharpness, absorbance, transmittance, contrast, and combinations thereof. If the measures are acceptable, the captured transient image is retrieved and can be processed for analysis of the intensity of the visual zones. The software may be configured to sequentially assess brightness and brightness gradients within the viewport area (12). Preferably the software is configured to sequentially assess also for the viewport area (region of interest) for darkness areas (photographic shadows). The software may be further configured to sequentially assess not only brightness, brightness gradient, shadow (dark areas) but also for reflections (areas of isolated high brightness) and sharpness.

Following retrieval of the saved image, the image can be corrected for any misalignment based on the control (C) or reference image (14) on the test cassette (10). It is advantageous to do this step after the assessment of the primary light parameters. Other than in the prior art, the terminal does not acquire images which do not fulfil the predetermined criteria for the measures of light as those cannot be corrected in arrear when a quantification must be done of the intensity of the visual zones. Accurate and predetermined measures of light are essential for a quantitative determination of an analyte by lateral flow chromatography. A subsequent correction of the light properties after image acquisition is always arbitrary and prone to error when the camera software is first preparing a "nice picture" in accordance with photographic criteria. Only an appropriate brightness around and on the visual signals (12) corresponding to control (C) and analyte (T)—and for reference images (14) on the test cassette (10) as well—allow for a true assessment and quantification of the concentration of analyte in the sample.

As mentioned, the reference images (14) may be machine-readable representations of data, e.g. a one or more bar codes and QR codes. The machine-readable data may comprise calibration information, lot number and/or expiration date but it is preferred that the machine-readable data provides the information for accessing a server so that all these data can be exchanged and retrieved from the cloud. The system software may also be configured to transmit acquired image data and test data to a remote processing device. In case of personal data, the system should be provided with certificates and authentication data for a coded transmission of information.

The mobile processing device (16) may be configured to retrieve, save, and/or process an uneven number of images of the viewport and lateral flow test, preferably from 1 to 13 images, more preferably from 3 to 11 images, most preferably from 5 to 9 images, so that the median value for the test zone, more precisely the median T/C, can be used as final test result. Other than prior art, the disclosed system and software does not capture multiple images at different exposure settings and does not combine those to create an image with a "higher dynamic range". In other words, the disclosed system relies on the assessment of an actual image and images with exceptional measure of light and reflections will finally be ignored by choosing the median of a plurality of captured and processed images.

The processor (16c) of the hand-held terminal and processor device (16) may be configured with an allowable for the luminance or brightness on the test cassette (10) or viewport. This implies that the software and device is configured to reject an image only when the measures of light and the luminance within the relevant region are outside the allowable range and/or varies in vertical and longitudinal direction. The allowable error may also be determined from the reference images (14) on the test cassette (10) but this is less preferred because it does not take account of the wetness of the lateral flow chromatography.

In another embodiment, the processor (16c) may be configured to identify the location of zones for control (C) and analyte (T) and perform peak searching to quantify the intensities of the zones for control and target, to determine their ratio either via peak height (preferred) or peak area (integrated signal) or any Gaussian range of the peaks. The concentration of the analyte in the test sample is then determined by correlation with corresponding calibration values.

The disclosure also relates to software for use in a smart phone (16). The software is configured to analyse transient image data to evaluate the distance between the digital camera (16a) and a reference image (14), and if within allowable range, said software is configured to analyse the transient image for the measures of light (luminance, brightness, brightness gradient) within the relevant region of said chromatography strip. Said software is configured to reject any transient image data when the evaluation of the measures and properties of light reflected from said chromatography strip is outside an allowable range, so that images and image data will be retrieved and saved for quantitative analysis of the presence of the analyte, which image data have been pre-examined as acceptable with respect to visual properties.

In a preferred embodiment, the camera is a phone camera. Another aspect of the invention is therefore a system for telemedicine based on a lateral flow test as described. The system for telemedicine comprises a smart phone application (software) for taking and pre-examining transient images, raw colour digital images, and a machine-reading of data codes and matrices provided on the housing of the lateral flow test. The permanent data will be used for authentication of the user to access the server and to download a standard curve and calibration data. The system for telemedicine may comprise facultatively a forwarding of the result of the lateral flow test device to a medical centre for patient monitoring, final verification and/or diagnoses, notably with respect to a further medication of the patient.

The software may be used with any handheld terminal having a camera and a source of light. The only other requirement is that the processor device must allow an examination of a sequence of transient images (video sequence) which is primarily a software and no hardware issue. The system can theoretically be used with any commercially lateral flow test with visual bands or signal zones. In practise, the lateral flow test must be standardized most carefully with respect to a constant thickness of the membrane and the separation material thereon as well as with respect to the application pad, the conjugation zone, and the zones with the immobilised receptors. The marker dye must further be selected for producing a visual signal adequately and proportionally. For the sake of accuracy and safety, each POCT may require a machine-readable data matrix or bar code for lot identification so that lot-specific calibration data can be used. The image with the region of interest of the POCT or rapid test is finally retrieved and saved by the processor or camera. The footage is usually returned by the camera in the form of spatially resolved RGB values. This means that for each pixel a value for red, green, and blue is delivered. The calculations can be performed in RGB, HSV, HSL, Lab, CMYK, or any other colour space.

Normalization of the image and elimination of any rotational error can be done in arrear as this merely requires a movement of pixels in accordance with some algorithms. This can be done via a pictogram of the cassette with some pre-programmed virtual pictogram. Other characteristic features of the POCT cassette, which can be used for alignment, are a) print-ons on the cassette such as i) corporate logos ii) captions, iii) machine-readable fonts and batch designations; b) geometric and characteristic borderlines of the test cassette itself such as: i) outside edges, ii) inside edges, and other iii) protrusions of the test cassette. The recorded image may be present at least in a resolution which is sufficient to analyse the visual signal with no distortion. Since the visual signal or zone can be found using the fixed geometric variables of the lateral flow test the orientation of the camera to the lateral flow test can be corrected without impacting the analysis of the visual zones.

The resolution of the cameras is of lesser importance when the intensity ratio (T/C) of the visual zones is used as wells as any rotational misalignment or skew. All fixed information relating to lengths, distances or sizes on the lateral flow test can be pre-programmed and adapted in the software as each lot of devices will require calibration and consequently also an adaptation of the according to the respectively supplied image resolution for each case. scales and proportions.

In order to initially assess the suitability of a transient image: 1. The mobile terminal or processor will independently decide whether the test cassette is correctly distanced to the camera and then batch-specific values will be measured as to the measures of light or the brightness and brightness gradient on the transient image. The implementation may include a registration of the position and size of the machine-readable batch information as well as the size and position of the printed company logo. 2. The user may also check the positions of both relative to the camera based on an overlay displayed on the screen. If brightness and overlay match, this will automatically trigger the recording of the transient image for further analysis of the visual zones. 3. A combination of points 2 and 1 is also contemplated, in which the image of point 2 is checked by the methods of point 1 and, if not satisfied, the image is normalized (scaled, rotated, shifted, or distorted) until the applicable criteria are fulfilled.

A person skilled in the art will appreciate that the framework around the openings and the markers can be used as well to determine focus, skew, positioning, distance, size, and other parameters. The cassette may further have printed on an individual test code in the form of a barcode or a two-dimensional quick reading code (QR) to allow of an external calibration (standard curve).

In a typical embodiment, the lateral flow test for quantitative determination of an analyte in a test sample comprises in fluid communication a sample pad for receiving the sample, a filter pad for filtering the sample and homogenization of the flow-through in wicking direction, a conjugate pad comprising mobile immunoreactants conjugated to a label, a membrane with porous separation material thereon, and a water-adsorptive wicking pad, wherein the separation membrane defines at least one first test zone comprising immobilized capture molecules for the analyte and one second test zone comprising immobilized capture molecules for labelled immunoreactant. It is preferred for the disclosed system that the conjugate pad comprises at least two types of labelled, but immunogenically and functionally distinct mobile immunoreactants, one mobile immunoreactant binding to the analyte to form a labelled complex and the other being inactive with respect to the formation of a complex with the analyte, so that this label reaction in the second test zone will be independent from the reaction of the other labelled immunoreactant with the analyte and the capture of the labelled complex in the first test zone, and whereas the inactive labelled immunoreactant is provided in the conjugate pad in a predetermined amount so as to provide an internal reference (C).

The lateral flow immunoassay format may be chosen from antigen sandwich assay, antibody assay, or competitive hapten assay. In a preferred embodiment, the lateral flow assay is incorporated in a cassette or envelope with defined openings for an application of test sample on the sample pad and for a photographic image of the test zones in a view port. As will be appreciated by a person skilled in the art that the immobilised immunoreactants within the first detection zone may be within two or more lines within the first test zone to provide for a more dynamic range of detection for the analyte. In a most preferred embodiment, the cassette has printed markers which indicate the one or more positions of the first test zone and optionally a marker which indicates the spatial arrangement of the second test zone comprising an internal reference (C) for a proper assessment and evaluation of the zones. In one embodiment, the protein is introduced to the sample pad using a dipstick format and contacting one end of the test device with the protein.

In another embodiment, the protein is applied onto the sample pad using an applicator, for example, a pipette, a syringe, a dropper, etc. The applied amount of fluid is preferably between about 1 and 200 µL, more preferably between about 3 and 100 µL, and most preferably between about 5 and 50 µL. The sample fluid may be selected from the group comprising buffered saline solution, pharmaceutical composition, and biological fluid. The biological fluid directly applied onto the sample pad may be selected from a group comprising blood, plasma, stool extract, faeces fluid, urine, lacrimal fluid, sweat, saliva, and amniotic fluid. The test sample may be a biological fluid of animal or plant origin. The sample fluid may also be processed food and/or mixtures of animal and plant material.

In one embodiment, the conjugate pad of the lateral flow test comprises a detectable marker. The detectable marker in the conjugate pad may be capable of binding the analyte applied on the sample pad. The conjugate pad may further ensure a uniform transfer of the detectable marker and the proteins (analytes) onto the test membrane. In another embodiment, the detectable marker comprises, but is not limited to, particles, luminescent labels, calorimetric labels, fluorescent labels, chemical labels, enzymes, radioactive labels, metal colloids, and chemiluminescent labels. Gold colloidal spheres are most preferred, while other metal sols and latex microparticles may be used as well. Photostable, colour tuneable nanoparticles such as carbon, selenium, or quantum dots have also been used as detectable markers. The detectable marker may also be a secondary protein, e.g. an enzyme, which catalyses a detection reaction, e.g. a colour-reaction.

As mentioned. the test membrane comprises at least one test zone and at least one control zone. Two or more test lines with the test zone may be used when there is a need for an increase quantifiable detection range. The one or more test lines (zone) must be of course upstream of the control zone.

In one embodiment, the analyte testing device may display (a) an individual code which is a barcode or a quick reading QR code, (b) framed openings within a cassette for either access to the sample pad and visual control of the test zones on the membrane, (c) markers on the cassette indicating the locations of the first test zone and the second test zone and (d) a defined area for performing a white balance. The individual code may have e.g. encoded the production lot and the QR-code the data for the calibration and interpretation of the test zone, so that the hand-held camera and processor device is enabled for a stand-alone operation, without internet connection, provided that all other can be downloaded in advance.

Another aspect relates to a method of determining the amount or concentration of an analyte in a test sample using a lateral flow immunoassay, the method comprising: (a) taking a digital image of the lateral flow immunoassay using a camera; (b) analysing the digital image for the location of the second test zone and determining the actual amount of label found in the second test zone on basis of the digital image; (c) comparing the actual amount of label found in the second test zone with a target amount of label in the second test zone to determine the offset of the digital image of the second test zone for one or more colour channels from their respective target values as determined by a calibrated digital image of the second test zone; (e) correcting the actual digital image on basis of the determined offset and further performing a white balance to adjust for the colour temperature of the ambient light and/or supportive flashlight and, optionally, of the optical properties of the camera and lenses used for the taken digital image; (f) analysing the offset-corrected digital image for the location of the first test zone and performing a quantitative determination of the label found in the first test zone; and (g) determining the amount of analyte contained in the test sample by comparison with the values of a series of calibrated standards as determined by lateral flow immunoassays of the same lot of production.

The following examples are provided to further illustrate the disclosure but are not intended to limit the scope of the invention. While they are typical of those that might be used, other procedures, methodologies or techniques known to those skilled in the art may alternatively be used.

EXAMPLES

Example 1—Test Analysis

A lateral flow test (12) was performed in a test device (10) bearing reference images (14); cf. FIG. 1A,B. Upon appearance of visible signals (T,C bands), the hand-held processor device was directed to the test cassette and a software application for image capturing was run using the digital camera (16a). It was first searched for a bar code (14) whether the lateral flow test was of an allowed production lot. When the reference image (14) was found, the distance between the mobile processor device and lateral flow chromatography was assessed based on reference images (14) on the test cassette. This was done on basis of the boundaries of the "viewport". Then the brightness and brightness gradient within the viewport was determined whether it contained any untypical dark areas (shadows). If the brightness within the viewport proved acceptable on the transient image, a gross section of the viewport was excised from the transient image, retrieved, and saved. Simultaneously, it was indicated to the user by a noticeable click that an image has been captured. Then any misalignment or skew of the saved image was corrected on basis of the control line (C) and the boundaries of the viewport. The saved and processed image was further processed for a determination of the peak intensities of the control and test lines (T, C) and then their ratio determined.

More precisely, the transient image was evaluated using multiple metrics, namely brightness gradient, brightness, shadow and facultatively, reflection and sharpness. When a metric was found outside the normal range, an error value was assigned, and the transient image became not used. When the image matched requirements, the relevant portion of the image was cut out and normalized, noise reduced, transformed into a relative "grayscale" (mean of the RGB) and, finally, the concentration of analyte determined based on the intensity ratio of the signal zones (T, C). When there was an error on the transient image, this was not communicated to the user but simply the transient image discarded. After a definite number of total errors, the user obtained support based on the rated images. This helped to draw conclusions about the environment and the test itself. Solutions to avoid these errors were communicated to the user.

Transient Images were constantly taken (about 4 frames per second) and each transient image analysed continuously in the image stream until a number of evaluable transient images could be retrieved and saved, that is, displaying acceptable light reflection and brightness metrics (outside predetermined error value ranges). Commonly, seven acceptable and evaluable transient images were retrieved, the relevant portions cut-out and analysed as described, from which one result corresponding to the median value was chosen and the result reported.

Example 2—Determination of Faecal Calprotecin

Markers such as anti-*Saccharomyces cervisiae* antibody (ASCA) or perinuclear anti-neutrophil cytoplasmic antibodies (p-ANCA) in serum and feacal calprotectrin have become integral components for monitoring the therapy of inflammatory bowel disease. Calprotectin is part of the body's non-specific immune system and released into circulation, bodily fluids and feaces by specialised immune cells (granulocytes). The calprotectin content in faeces is a marker for inflammation of the intestinal wall and its measurement is ideally suited for assessing the disease activity of gastrointestinal diseases such as inflammatory bowel disease (IBD), Crohn's disease, or ulcerative colitis. Monitoring of neutrophilic inflammation markers (calprotectin, lactoferrin) facilitates early recognition of a recurrent disease flare following established remission or initially successful surgical intervention. It is also the first method to allow non-invasive monitoring of therapy response in terms of muosal healing, allowing a more prompt stepping-up of therapy when indicated. Monitoring a stool analyte cannot be done easily in the doctor's office and the logistics are most complicate in addition to patient's embarrassment and lack of compliance.

The analyte testing system was made up of a modified and adapted test device (Preventis®, Bensheim, Del.) and a software package. The test device was adapted, standardized and modified for a quantitative determination of calprotectin in faeces. This required that the calibration curve for the assessment of the bands was saved on a server which could be assessed on basis of the software registration and the code for the production lot. In brief, the Preventis® test device consisted of an immunological rapid test for detection of human calprotectin via gold-conjugated anti-calprotectin antibodies, which further comprised a pre-determined amount of non-analyte specific antibody in the conjugation pad to achieve a standard intensity of the control zone (C) independently from the amount of calprotectin in the analyte. The result of the rapid test was quantitatively assessed based on the ratio of the peak intensities of the lines for control (C) and tested analyte (T). Seven transient images were retrieved, saved, processed and assessed using the deposited lot-specific calibration data. The additional reference image (QR-code) comprised an authentication and confidentiality data and the respective smart phone had to be registered with the server together with a code handed-out by the supervising physician. Date, time and result (median) were automatically sent to the patient's supervising physician and displayed to the user. The test could cover a measuring range from 25 to 2000 µg calprotectin/g stool. Across that range of calprotectin concentrations, the rapid test was able to identify those patients with inflammatory activity in the bowel with a degree of certainty comparable with the laboratory reference method.

In brief, the packaging comprised the following other items: stool catcher, sample collection tube with extraction buffer, test cassette in sealed aluminium pouch and a leaflet with instructions. The cap of the sample collection tube was unscrewed and the sample collection stick removed. Then, in one go, the sample collection stick was inserted into the stool sample at 3 different points and ensured that the grooves (volume for roughly 10 mg stool) at the bottom tip of the collection stick were filled with faeces. The collection stick with the adhering faeces was returned into the sample collection tube containing extraction buffer solution. Additional stool was stripped off by grooves in the cap. A repeated transfer of stool into the sample collection tube compromised the test performance. For this reason the sampling stick could be only used once. After gentle shaking, the stool sample solution was filtered through a sieve and could be used immediately.

The test cassette was removed from the aluminium pouch and placed on a flat, dry surface. The sample collection tube was shaken gently for a few seconds and the bottom tip broken off. Four drops of extraction buffer with sample were applied onto the sample application window on the test cassette by evenly squeezing the sample collection tube, and then immediately pressed "start timer" in the software app. After 15 minutes the lateral flow chromatography was complete and could be analysed.

For taking an image, the test cassette was placed on a bright, flat and smooth surface. Shadows, strong light from the side and direct sunlight should be avoided. A template of the test cassette was shown on the screen of the mobile phone. The test device was aligned in front of the user with the template on screen. While doing this, the mobile phone was kept horizontally, parallel to the test cassette, and tilting was avoided. The Preventis app automatically triggered the camera and went to the "analysis screen" which was actually a video screen (four frames per second) until seven suitable transient images with correct brightness in the viewport region and distance were found. Once the image taking was complete, the saved images were analysed and the median result was shown on the mobile phone's screen. The result was also sent to the doctor automatically, in pseudonymised form to protect personal data. Consequently, the patient was enabled to determine and record the disease status independently from the physician and the supervising medical centre or the general physician also received the data for a prompt stepping up of the therapy in case of a disease flare.

REFERENCE SIGNS

10 Test device
12 Lateral flow test, viewport, region of interest
14 Reference image
T Test zone, responsive zone
C Control zone, control
S Sample pad
16 Portable processor device
16a Digital camera
16b Source of light
16c Processor
18 Casing
20 Reagents
22 Digital display

The invention claimed is:

1. A system for determining the presence and content of an analyte in a test sample subjected to lateral flow chromatography, the system comprising
  a test device adapted to house a lateral flow test, wherein said test device further displays one or more reference images and a region of interest of said lateral flow test which bears one or more visible response zones indicating the presence and content of said analyte in said test sample and a control zone, and
  a portable processor device comprising a digital camera, a source of light and a processor, wherein said processor is configured to process transient digital images of a video captured by said camera and to represent an analytical result, wherein:
  said processor is configured to analyze sequentially a plurality of the transient digital images of the video for the presence of one or more permanent reference images;
  said processor is configured upon finding one or more permanent reference images, to determine the distance between the found permanent reference image and the digital camera to determine if the distance is acceptable;
  said processor is configured to analyze each transient digital image of the video having said permanent reference image at an acceptable distance for said region of interest; and
  said processor is configured to examine each of said regions of interest of each transient digital image of the video having a permanent reference image at an acceptable distance for its measures of light reflected and, if the light reflected is in line with predefined measures, said processor is configured to retrieve and save said transient digital image so that only digital images of the region of interest will be processed and analyzed for the optical intensities of said zones which are based on predefined light conditions.

2. The analyte testing system as claimed in claim 1, wherein the processor is configured to determine the measures of light with respect to absolute brightness, brightness gradient, areas of dark pixels (shadows) and combinations thereof.

3. The analyte testing system as claimed in claim 1, wherein the processor is configured to retrieve and record multiple approved transient image data of the region of interest for determining the optical intensities of said visible zones.

4. The analyte testing system as claimed in claim 3, wherein the recorded digital images of the region of interest are corrected for any degree of error associated with any rotational misalignment or skew of the visible zones prior to determination of the optical intensities of the visible zones.

5. The analyte testing system as claimed in claim 1, wherein the lateral flow test comprises a predetermined amount of control to achieve a defined control zone independently from the presence and content of the analyte in the test sample.

6. The analyte testing system as claimed in claim 1, wherein the processor is configured to determine the intensity ratios of the zones from a number of saved images and chooses a median ratio for quantitative analysis of the analyte in the test sample.

7. The analyte testing system as claimed in claim 1, wherein a displayed reference image contains a machine-readable representation of data which encodes or provides access to characteristic data of the lateral flow test.

8. The analyte testing system as claimed in claim 1, wherein the portable processor device is configured to exchange data and image data with a remote server.

9. The analyte testing system as claimed in claim 1, wherein the processor is configured to employ data on sharpness and contrast of a displayed reference image.

10. The analyte testing system as claimed in claim 1, wherein the processor is configured to employ data on the location of the displayed reference image to identify the location of the region of interest with the visible zones.

11. The analyte testing system as claimed in claim 1, wherein the test device comprises a lateral flow test adapted for faecal calprotectin, serum calprotectin, vitamin D in blood or serum, luteinizing hormone, follicle stimulating hormone, chorionic gonadotropin, thyroid stimulating hormone, albumin, faecal occult blood, gluten immunogenic peptides, bladder cancer marker, *Mycobacterium tuberculosis, Mycobacterium bovis, Mycobacterium africanum, Helicobacter pylori*, Influenza virus A and B, troponin I, Tinea unguium, ferritin, D-dimer, C-reactive protein, group A *Streptococcus*, group B *Streptococcus*, genetically modified organisms, allergens present in cereals and products thereof, chickpea and products thereof, peanut and products thereof, hazelnut and products thereof, macadamia and products thereof, mustard and products thereof, soya and products thereof, sesame and products thereof, walnut and products thereof, pistachio and products thereof, lupin and products thereof, celery and products thereof, fish and products thereof, crustaceans and products thereof.

\* \* \* \* \*